(12) United States Patent
West (10) Patent No.: US 11,446,212 B2
(45) Date of Patent: Sep. 20, 2022

(54) MULTIPLE CAVITY CARRIER APPARATUSES FOR DETECTING REMOVAL OF ITEMS FROM CAVITIES AND THEIR REPLACEMENT

(71) Applicant: Embecta Corp., Andover, MA (US)

(72) Inventor: Robert West, Basking Ridge, NJ (US)

(73) Assignee: Embecta Corp., Andover, MA (US)

( * ) Notice: Subject to any disclaimer, the term of this patent is extended or adjusted under 35 U.S.C. 154(b) by 89 days.

(21) Appl. No.: 16/964,612

(22) PCT Filed: Jan. 15, 2019

(86) PCT No.: PCT/US2019/013599
§ 371 (c)(1),
(2) Date: Jul. 24, 2020

(87) PCT Pub. No.: WO2019/152181
PCT Pub. Date: Aug. 8, 2019

(65) Prior Publication Data
US 2020/0375852 A1 Dec. 3, 2020

Related U.S. Application Data

(60) Provisional application No. 62/625,155, filed on Feb. 1, 2018.

(51) Int. Cl.
*G08B 1/00* (2006.01)
*A61J 7/04* (2006.01)
(Continued)

(52) U.S. Cl.
CPC .......... *A61J 7/0436* (2015.05); *A61J 7/0015* (2013.01); *A61J 7/0084* (2013.01); *A61J 7/0445* (2015.05);
(Continued)

(58) Field of Classification Search
CPC ...... A61J 7/0436; A61J 7/0015; A61J 7/0084; A61J 7/0445; G16H 20/13
(Continued)

(56) References Cited

U.S. PATENT DOCUMENTS 5,239,491 A     8/1993   Mucciacciaro
5,273,161 A  *  12/1993  Sagstetter ........ A61B 5/150389
                                                    220/908
(Continued)

FOREIGN PATENT DOCUMENTS

CN       101703816 A     5/2010
CN       210698382 U     6/2020
WO       2017035474 A1   3/2017

OTHER PUBLICATIONS

International Search Report dated Jun. 17, 2019, which issued in counterpart PCT Patent Application No. PCT/US2019/013599.

*Primary Examiner* — Tai T Nguyen
(74) *Attorney, Agent, or Firm* — Greenberg Traurig, LLP; David J. Dykeman; Roman Fayerberg (57) ABSTRACT

Devices, systems and methods are provided to detect when items are removed from a multiple cavity carrier (MCC) that stores items (e.g., pen needle assemblies) in respective cavities. A separate, reusable data collection unit (DCU) can be mounted to the MCC and has sensors for detecting cavity status (e.g., empty or filled with an item). The DCU stores data related to time stamps, optional dates, and cavity locations of item removal from and optional used item return to respective ones of the MCC cavities to help users track item usage (e.g., pen needle assemblies) to improve medication delivery management such as insulin injections with an injection pen and pen needle assemblies. Indicators can be generated to indicate from which cavity the next item should be extracted to encourage injection site rotation.

15 Claims, 8 Drawing Sheets

(51) Int. Cl.
*G16H 40/63* (2018.01)
*G16H 20/13* (2018.01)
*A61J 7/00* (2006.01)

(52) U.S. Cl.
CPC ............. *G16H 20/13* (2018.01); *G16H 40/63* (2018.01); *A61J 2200/70* (2013.01)

(58) Field of Classification Search
USPC .................................................. 340/309.16
See application file for complete search history.

(56) References Cited

U.S. PATENT DOCUMENTS

| | | | |
|---|---|---|---|
| 5,741,230 A * | 4/1998 | Miller | A61L 2/04 604/110 |
| 9,728,068 B2 | 8/2017 | Engelhard et al. | |
| 2008/0117053 A1 | 5/2008 | Maloney | |
| 2008/0289973 A1 | 11/2008 | MacLeod | |
| 2012/0041390 A1 | 2/2012 | Spool et al. | |
| 2012/0228192 A1 | 9/2012 | Niven | |
| 2014/0277707 A1 | 9/2014 | Akdogan et al. | |
| 2016/0022361 A1 | 1/2016 | Khajavi | |
| 2016/0210439 A1 * | 7/2016 | Hartlaub | A61J 7/0084 |

* cited by examiner

MULTIPLE CAVITY CARRIER APPARATUSES FOR DETECTING REMOVAL OF ITEMS FROM CAVITIES AND THEIR REPLACEMENT

BACKGROUND OF THE INVENTION

Field of the Invention

Illustrative embodiments of the present invention relate generally to a multiple cavity carrier and enhancements to a multiple cavity carrier for detection of removal of components from respective cavities and return of components to the cavities.

Description of Related Art

A multiple cavity carrier has been proposed for storing and dispensing, for example, needle assemblies used with hypodermic syringes. The needle assemblies can include, for example, pen needles that are configured to attach to an adapter with threads that mate with threads on a medication delivery pen. An example of a multiple cavity carrier is a pen needle magazine dispenser for holding a plurality of pen needle assemblies such as those described in commonly-owned U.S. Pat. Nos. 5,829,589, 5,873,462 and 6,346,094, the contents of which are incorporated herein by reference.

Prior systems for detecting removal of an item from a cavity in a multiple cavity carrier and its return to the cavity have employed disposable radio frequency identification (RFID) labels or tags on the item. Such use of RFID labels or tags can be costly and can unnecessarily add complexity to the multiple cavity carrier, which must be provided with an RFID tag reader.

SUMMARY OF THE INVENTION

The above and other problems are overcome, and additional advantages are realized, by illustrative embodiments of the present invention.

Apparatuses are provided for improving a multiple cavity carrier (MCC) and the information it provides to a user regarding the storage and, optionally, the replacement of items therein. An improved multiple cavity carrier uses more cost effective and less complicated methods of detecting items in cavities of a MCC than RFID tags and corresponding RFID reader(s). Also provided are improved indications to a user regarding which item to remove next from the MCC for use.

In accordance with aspects of illustrative embodiments, a reusable data collection unit is provided that is detachably connected to a dispenser, the dispenser having cavities configured to enclose respective items for storage therein and subsequent removal, the data collection unit comprising: a base housing detachably connected to the dispenser; plural sensors provided on the base housing and configured to detect presence and absence of the items in the respective cavities and generate corresponding sensor data; a memory device configured to store the sensor data; and a processor provided in the base and configured to analyze the sensor data and determine a time stamp of removal of the items from respective ones of the cavities.

In accordance with aspects of illustrative embodiments, a medical instrument dispensing device is provided having a reusable data collection unit detachably connected to a dispenser, the dispenser having cavities configured to house a plurality of sterile medical instruments for storage therein and subsequent removal, the data collection unit comprising: a base housing detachably connected to the dispenser; plural sensors provided on the base housing and configured to detect presence and absence of each of the plurality of sterile medical instruments in the corresponding cavity and generate corresponding sensor data; a memory device configured to store the sensor data; and a processor provided in the base and configured to analyze the sensor data and determine a dataset to characterize the removal of at least one of the plurality of sterile medical instruments from its corresponding cavity.

In accordance with aspects of illustrative embodiments, the processor is configured to analyze the sensor data and determine a dataset comprising at least one of a date and a time of removal of the items (e.g., such as sterile medical instruments) from respective ones of the cavities.

In accordance with aspects of illustrative embodiments, the processor is configured to analyze the sensor data and determine a dataset comprising at least one of a date and a time of return of the items (e.g., such as sterile medical instruments) to respective ones of the cavities.

In accordance with aspects of illustrative embodiments, the dispenser is a pen needle magazine dispenser and the items (e.g., sterile medical instruments) are pen needle assemblies.

In accordance with aspects of illustrative embodiments, the cavities are arranged in a designated pattern in the dispenser, and the sensors are arranged in the base housing in a similar pattern to align the sensors with the cavities when the dispenser is connected to the base housing.

In accordance with aspects of illustrative embodiments, the plural sensors create a sensor matrix in the base housing, and the cavities in the dispenser are configured in accordance with a grid pattern that corresponds to the sensor matrix.

In accordance with aspects of illustrative embodiments, the dispenser has a top separated from a bottom by a wall that defines an outer perimeter of the dispenser, and the cavities each extend from the top toward the bottom of the dispenser. The outer perimeter defines an anthropomorphic shape, and the cavities are disposed in areas within the anthropomorphic shape that correspond to proposed injection sites on at least one of a patient's arms, thighs, abdomen and buttocks. The processor is configured to analyze the sensor data and determine which of the proposed injection sites have been used based on detection of the absence of items from their corresponding cavities, and select the next proposed injection site based on a designated pattern for using the items on the patient, and generating an indication that indicates which of the items in the cavities to remove from the dispenser and use next on the patient.

In accordance with aspects of illustrative embodiments, the indication is at least one of a designated color and a flash of an LED.

In accordance with aspects of illustrative embodiments, the bottom of the dispenser comprises at least one transparent area that is aligned with at least one of the cavities, the corresponding one of the sensors aligned with the cavity being operable to detect ambient light that enters the cavity when the corresponding item is removed from the cavity.

In accordance with aspects of illustrative embodiments, the sensor data is transmitted from the reusable data collection unit to a remote device using at least one of a USB connector and a wireless link In accordance with aspects of illustrative embodiments, a dispenser is provided that encloses respective items for storage therein and for subsequent removal, the dispenser comprising: a first surface separated from a second surface by a wall that defines an outer perimeter of the dispenser; and a plurality of cavities, each cavity extending from the first surface toward the second surface of the dispenser and dimensioned to store one of the items. The first surface comprises a plurality of apertures corresponding to openings at a first end of each of the cavities and configured to receive one of the respective items into that cavity, and the second surface is a sensor transmissible surface that cooperates with a plurality of sensors in a data collection unit detachably connected to the dispenser to facilitate detecting the presence of an item in each of the cavities.

In accordance with aspects of illustrative embodiments, each of the cavities operates as a light pipe reflecting ambient light entering the apertures, the cavities being dimensioned relative to the items placed therein to prevent the ambient light from reflecting to the second surface when the item is in the cavity and allowing the ambient light to reflecting to the second surface when the item is removed from the cavity.

In accordance with aspects of illustrative embodiments, each of the cavities is provided with a lens adjacent the second surface that is configured to focus the ambient light through the second surface and to a photosensor of the data collection unit.

In accordance with aspects of illustrative embodiments, the lens is configured to implement an edge-ray principle of non-imaging optics.

In accordance with aspects of illustrative embodiments, the lens is configured to implement a compound parabolic concentrator.

Additional and/or other aspects and advantages of the present invention will be set forth in the description that follows, or will be apparent from the description, or may be learned by practice of the invention. The present invention may comprise multiple cavity carriers and methods for operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and/or other aspects and advantages of embodiments of the invention will be more readily appreciated from the following detailed description, taken in conjunction with the accompanying drawings, of which.

Throughout the drawing figures, like reference numbers will be understood to refer to like elements, features and structures.

DETAILED DESCRIPTION OF ILLUSTRATIVE EMBODIMENTS

Reference will now be made in detail to embodiments of the present invention, which are illustrated in the accompanying drawings. The embodiments described herein exemplify, but do not limit, the present invention by referring to the drawings.

Figure 1:
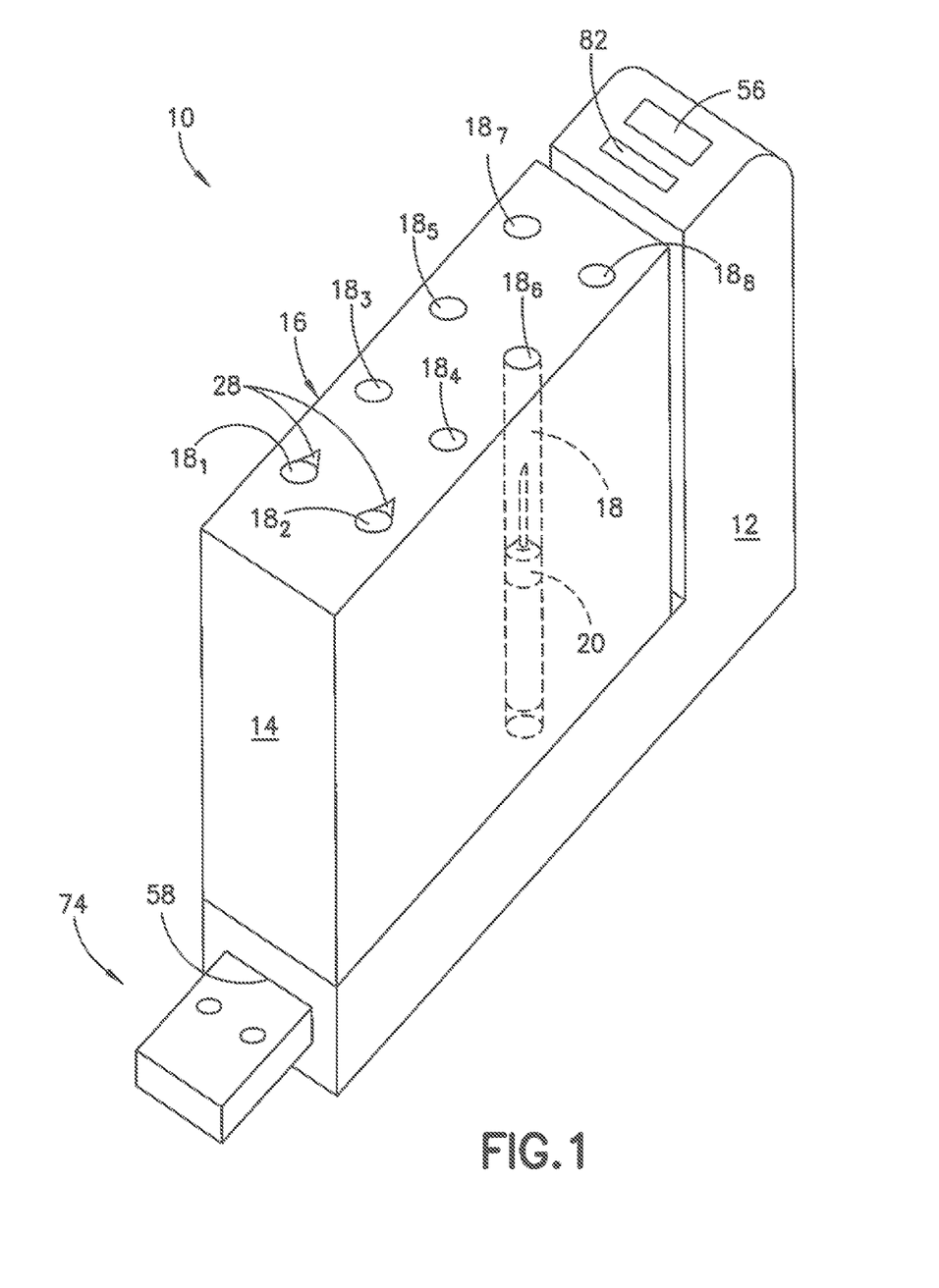
FIG. 1 is a perspective view of a smart dispenser constructed in accordance with an embodiment of the present invention.
Figure 2A:
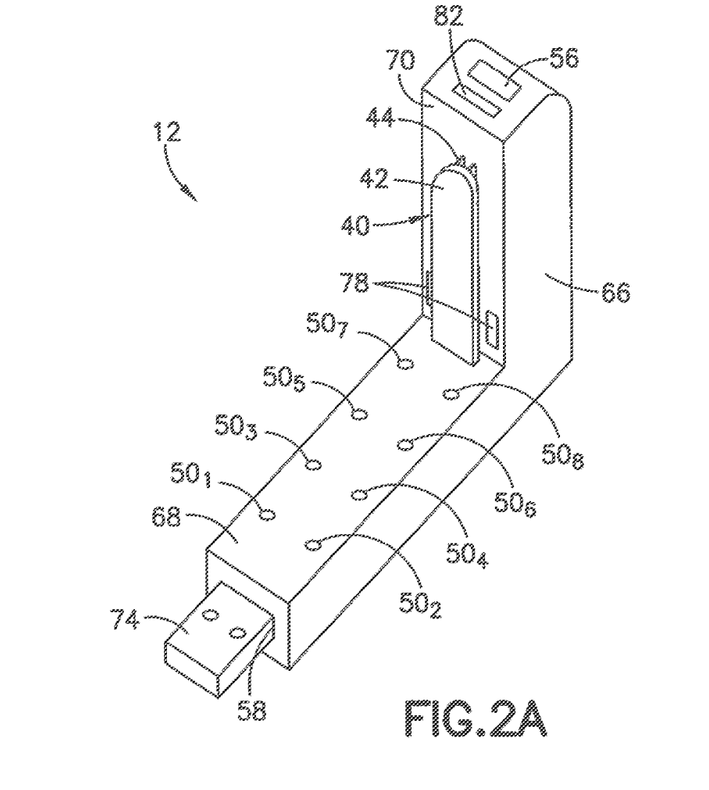
FIG. 2 is a perspective view of a data collection unit of the smart dispenser of FIG. 1 in accordance with an embodiment of the present invention.
Figure 2B:
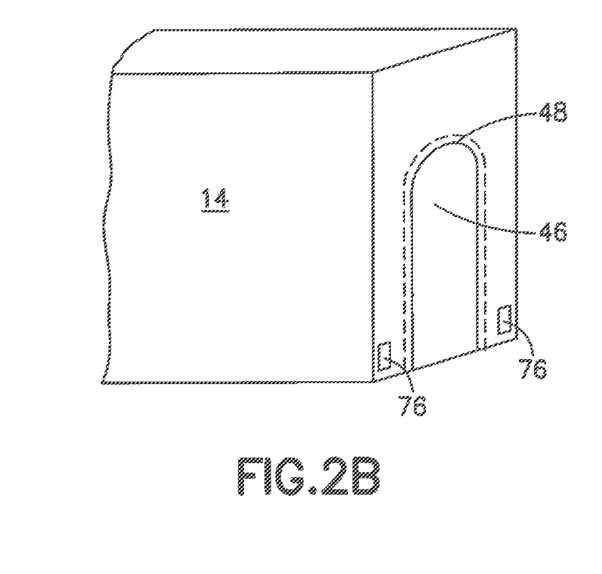

FIG. 1 illustrates an example embodiment of a smart dispenser 10 comprising a reusable data collection unit (DCU) 12 connected to a multiple cavity carrier (MCC) 14. The DCU 12 and MCC 14 are configured to allow detection of the removal of items 20 from, and return of items 20 to, respective cavities $18_1$-$18_n$ in a housing 16 of the MCC 14. In accordance with aspects of illustrative embodiments, the MCC 14 is detachably mounted onto the DCU 12. FIGS. 2A and 2B illustrate, respectively, the DCU 12 separated from the MCC 14.

Figure 3:
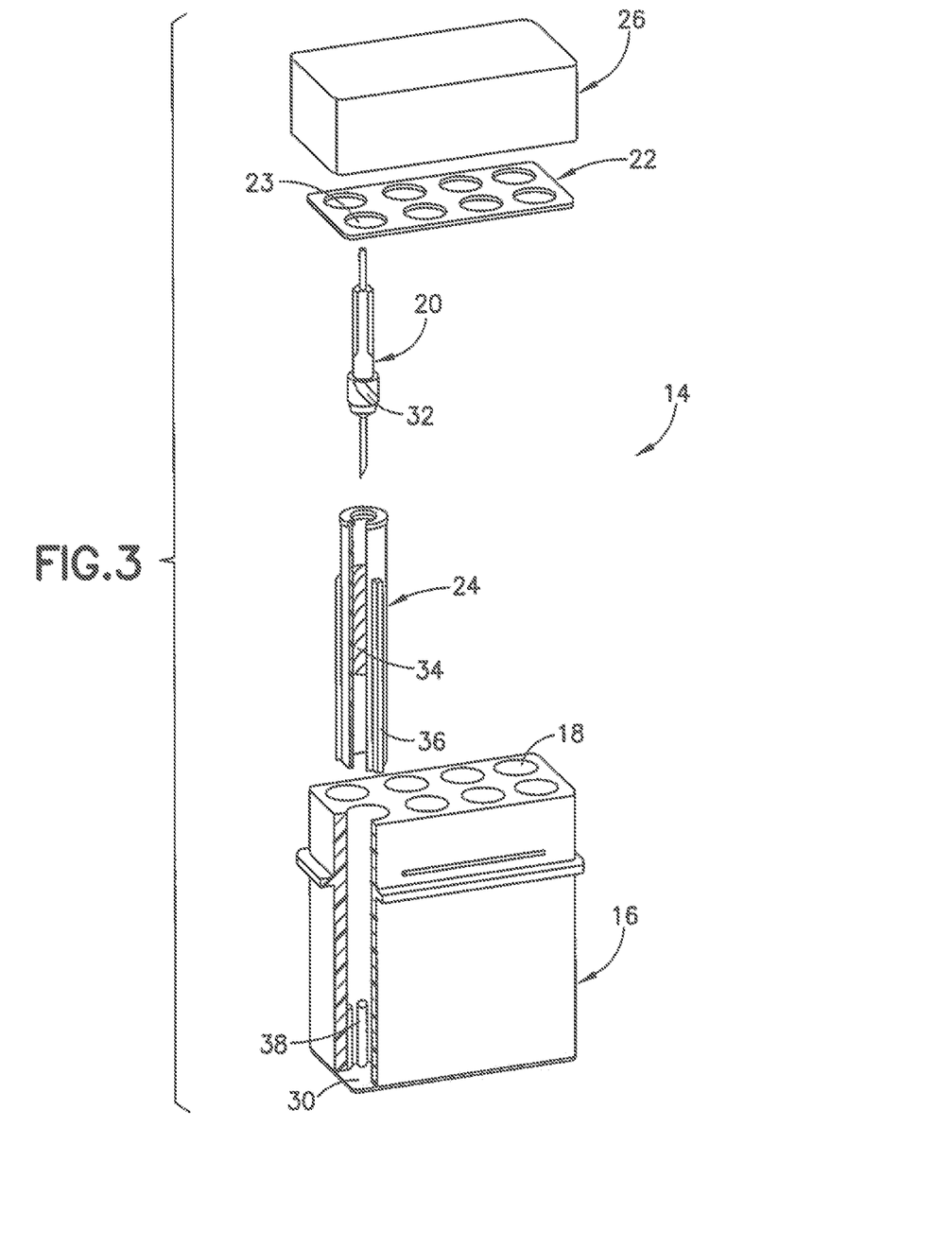
FIG. 3 is an exploded diagram of a multiple cavity carrier of the smart dispenser of FIG. 1 in accordance with an embodiment of the present invention.

With reference to FIGS. 1 and 3, the MCC 14 has a housing 16 with a plurality of cavities $18_1$-$18_n$ arranged in a grid or other pattern. Each cavity 18 in the housing 16 is dimensioned to receive an item 20 such as a pen needle assembly. For example, the MCC 14 can be a pen needle magazine that holds and dispenses sterile pen needle assemblies 20 for medication delivery pens and that safely stores the needles after use. It is to be understood, however, that the MCC 14 can be a carrier with cavities $18_1$-$18_n$ dimensioned for storing other types of items 20 besides pen needle assemblies, and that the DCU 12 can be configured to detect when items 20 are removed from respective cavities $18_1$-$18_n$ and can optionally detect when an item 20 is returned to its cavity 18.

Figure 6:
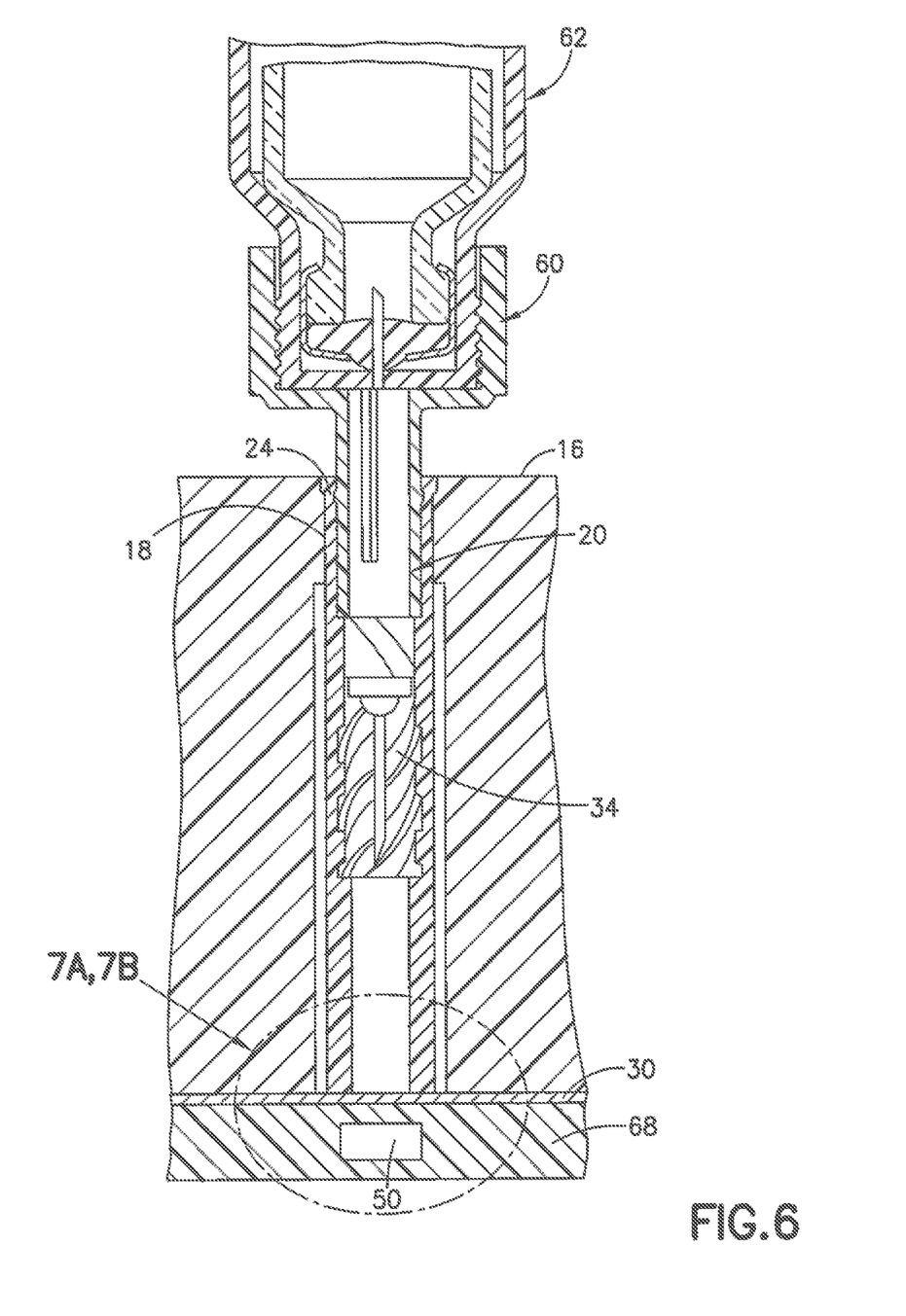
FIG. 6 is an cross-section view of a smart dispenser constructed in accordance with an embodiment of the present invention.

In accordance with an example embodiment wherein the MCC 14 is a magazine dispenser that stores pen needle assemblies 20 in its cavities $18_1$-$18_n$, a user can insert an adapter 60 on a medication delivery pen 62 into one of the cavities $18_1$-$18_n$, as shown in FIG. 6. The user rotates the pen 62 to mount an unused pen needle assembly 20 on the adapter 60 of the medication delivery pen. After an injection has been performed, the used pen needle assembly 20 is then returned to the cavity 18 by inserting the used pen needle assembly into the cavity and rotating the pen 62 to detach the pen needle assembly from the adapter on the pen. The example magazine dispenser is described in commonly owned U.S. Pat. No. 6,346,094 which is incorporated by reference herein in its entirety. It is to be understood, however, that the MCC 14 can be configured to receive other types of items besides pen needle assemblies, and that an adapter is not necessarily required to attach to an item 20 for its removal from and return to a cavity 18.

When a user inserts a medication delivery pen 62 or other device into one of the cavities $18_1$-$18_n$ of a MCC 14 and mounts an unused pen needle assembly 20 on the medication delivery pen, the resultant open or empty cavity 18 is detected by the DCU 12, and data regarding one or more of date, time and location of the detected open cavity 18 is recorded via a microprocessor and memory in the DCU 12, as described below in connection with FIG. 4. After an injection has been performed and the used pen needle assembly 20 is returned to the cavity 18, the resultant filled cavity is detected by the DCU 12, and data about the date, time and location of the detected filled cavity is recorded via the DCU's microprocessor and memory. Location can refer to physical location (e.g., GPS coordinates from a microprocessor), location on the MCC 14, or body location, or a combination of any of these. This recorded data is beneficial to a user for tracking medication delivery events. Further, as described below, the DCU 12 can provide indicators to help a user select the next item 20 from the MCC 14 to use to encourage injection site rotation. The devices for sensing empty and filled cavities $18_1$-$18_n$ in an MCC 14 and DCU 12 are described in more detail below.

As stated above and with reference to FIGS. 1, 2 and 3, the MCC 14 has a housing 16 with cavities $18_1$-$18_n$. In accordance with an illustrative embodiment, the housing 16 with cavities $18_1$-$18_n$ is provided with respective bullets $24_1$-$24_n$, and each bullet 24 is configured to line a corresponding cavity 18, as shown in FIGS. 3 and 6. The cavity 18 with or without a bullet 24 can operate as a light pipe to a sensor 50 (e.g., photosensor) in the DCU 12, as described below in connection with FIGS. 7A and 7B. It is understood that the DCU 12 can use different types of sensors 50 (e.g., a Hall effect sensor or other type of proximity sensor) besides photosensors and therefore the bullet 24, cavity 18 and portion of the housing adjacent to the cavity 18 need not operate as a light pipe.

The bullets $24_1$-$24_n$ can be detachable relative to the housing 16 and corresponding cavity 18 or formed as an integral part of the cavity 18. Advantages of having the bullets $24_1$-$24_n$ configured to be separate from and not integral to the housing 16 are that each bullet 24 provides an efficient mechanism to load a pen needle assembly 20 into the MCC 14, and it also provides for ease of manufacturing, inspection of individual pen needle assemblies 20 and improved quality control. In particular, if a damaged pen needle assembly 20 is found within a bullet 24, the entire bullet 24 and pen needle assembly 20 can be disposed of and replaced with a new pen needle assembly 20 and bullet 24 without loss of the remainder of MCC 14 housing 16 and the other pen needle assemblies 20. Further, this arrangement allows for easy manufacture of a large volume of bullets 24 to be incorporated into a variety of MCC's. The configuration of the bullets $24_1$-$24_n$ to facilitate detection of the removal and return of an item 20 therein by the DCU 12 is described below on connection with FIGS. 6, 7A and 7B.

By way of an example, as shown in FIG. 3, each of the bullets $24_1$-$24_n$ can be provided with threads 34 that interact with threads 32 provided on a pen needle assembly 20 to be inserted into that bullet. Each bullet 24 can also be provided with an anti-rotation rib 36 or other retention mechanism for mating with a groove 38 in a cavity 18 to at least detachably secure the bullet 24 in the cavity 18. Other retention mechanisms can be used to secure an item 20 in a bullet 24 or otherwise in a cavity 18. Further, other retention mechanisms can be used to retain a bullet 24 in a cavity 18 or, as stated above, the bullets $24_1$-$24_n$ can be integral with the housing 16 and not removable from respective cavities $18_1$-$18_n$.

The housing 16 and the bullets $24_1$-$24_n$ can be molded, for example, from Polypropylene or similar material. As illustrated in FIG. 3, the MCC 14 can be optionally provided with a cover 26 that can, for example, be snap fit or press fit onto the MCC 14 and removed when the MCC 14 is mounted on the DCU 12 as shown in FIG. 1. In addition, the MCC 14 can be provided with an integrated or be separate layer 22 on top of housing 16. The layer 22 can be formed from an opaque material, for example, to reduce the amount of undesired light that may enter the cavities $18_1$-$18_n$ when they are configured to operate as light pipes, and interfere with accurate detection of item 20 placement, removal, and replacement from a corresponding cavity 18 as described below. The layer 22 has apertures 23 aligned with respective cavities $18_1$-$18_n$ for receiving an item 20 and each of the apertures 23 can be provided with a sterility membrane or label 28, as shown in FIG. 1. In the example of a cavity 18 that receives a bullet 24 with an item 20 as described above, the bullets $24_1$-$24_n$ can each be provided with the sterility membrane or label 28. In either case, the sterility membrane or label 28 is removed when the item 20 (e.g., pen needle assembly 20 in the bullet 24) is about to be used. In the example embodiment depicted in FIG. 1, the MCC 14 has eight cavities $18_1$ through $18_8$ where cavities $18_3$ through $18_5$, $18_7$ and $18_8$ are empty (e.g., the item 20 stored in the cavity 18, such as a bullet 24 with a pen needle assembly 20 therein, has been removed), cavities $18_1$ e. $18_2$ are filled with an item 20 (not shown) and sealed with the sterility barrier 28, and cavity $18_6$ has its barrier 28 removed and is currently filled with an item 20 that is about to be removed. Alternatively, the layer 22 can be provided with a membrane layer 28 over most of its area (e.g., adhered to the layer 22), and the membrane 28 can be provided with indicia corresponding to and proximal with respective cavities $18_1$-$18_n$ to facilitate puncture of the membrane at the location of a cavity 18 when an item 20 is removed therefrom.

The DCU 12 has a housing 66 that, like the MCC 14 and bullets 24, can also be molded from Polypropylene or similar material. The housing 66 encloses sensors $50_1$-$50_n$ arranged in a similar grid or pattern to the cavities $18_1$-$18_n$ in the MCC 14 such that each sensor 50 can be used to detect the absence or presence of an item 20 in its corresponding cavity 18. The DCU 12 depicted in FIG. 2A, for example, has sensors $50_1$-$50_8$ arranged in a matrix to be collinear with the longitudinal axes of corresponding ones of the cavities $18_1$ ad $18_8$ in the MCC 14. Depending on the type of sensor 50 used, the sensors $50_1$-$50_n$ may or may not be visible on the surface 68 of the housing 66 that abuts the bottom layer 30 of the MCC 14 housing 16.

The surface 70 of the DCU 12 that abuts the side of the MCC 14 housing 16 is provided with a retention feature 40 that cooperates with a retention feature 46 on the MCC 14 to detachably mount the MCC 14 on the DCU 12. For example, the retention feature 40 can comprise a plate 42 raised from the surface 70 by a narrower neck 44. The plate 42 and neck 44 can be integrally formed in the housing 66. The retention feature of the MCC 14 comprises a recess 46 with lip 48 wherein the recess 46 is dimensioned to receive the plate 42 but the area defined by the lip is smaller than the recess to retain the MCC 14 on the DCU 12 when the lip 48 on the MCU 14 is slid behind the plate 42 and over the neck 44 of the DCU 12. Other retention mechanisms can be used on the DCU 12 and MCC 14 that cooperate with each other to detachably mount the MCU 14 on the DCU 12 such that the sensors $50_1$-$50_n$ in the DCU 12 are aligned with corresponding ones of the cavities $18_1$-$18_n$ in an MCC 14. It is to be understood that the retention features 40 and 46 can be deployed on other surfaces of the DCU 12 and MCC 14, respectively, than those illustrated in FIGS. 2A and 2B. In addition, the DCU 12 and MCC 14 can be provided, respectively, with one or more metal contacts 76 and magnet(s) 78 to provide a magnetic connection between the MCC 14 and DCU 12 and therefore more securely mount the MCC 14 on the DCU 12.

Figure 4:
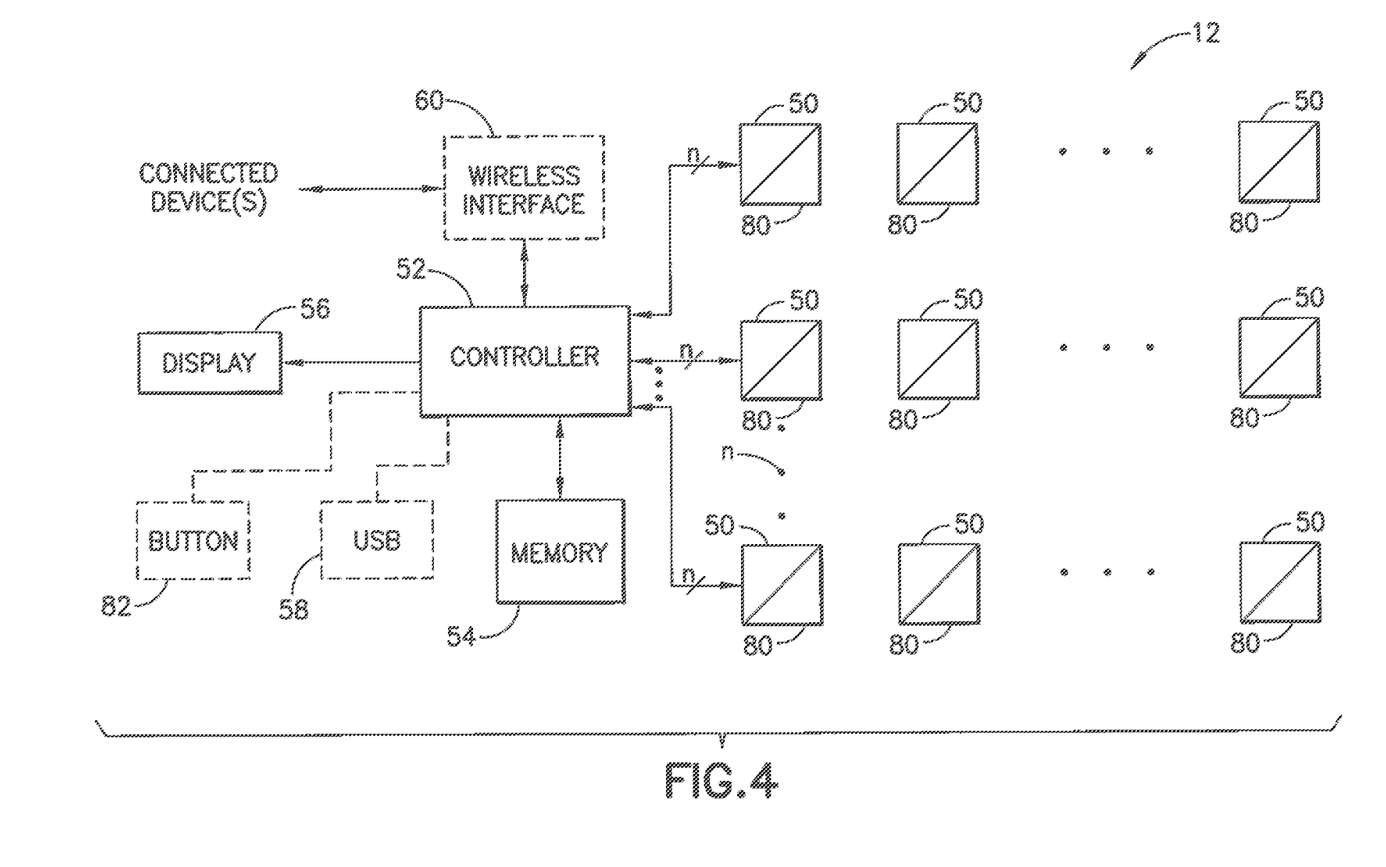
FIG. 4 is a block diagram of a data collection unit in accordance with an embodiment of the present invention.

With reference to FIGS. 2A and 4, the DCU 12 is provided with a microprocessor or other type of controller 52 and integrated and/or separate memory storage device 54 for storing data received from the plurality of sensors $50_1$-$50_n$. In accordance with an illustrative embodiment of the present invention, the DCU 12 can also be provided with light-emitting diodes (LEDs) $80_1$-$80_n$ or other indicators of status for respective ones of the cavities $18_1$-$18_n$ such as whether a cavity is empty, filled, is the next cavity 18 from which an item 20 should be removed for use, or an error has occurred, as described in more detail below. A display 56 is provided (e.g., a liquid crystal display (LCD)) such that the DCU 12 can be operated via the controller 52 to display selected data such as the date and time an item was removed and replaced within a designated time period, which can represent a deployment of an item 20 such as a pen needle assembly and therefore a corresponding administration of an injected medication by a medication delivery pen to which the pen needle assembly was connected and removed from a cavity 18 and then returned to the cavity 18 and disconnected.

Figure 5:
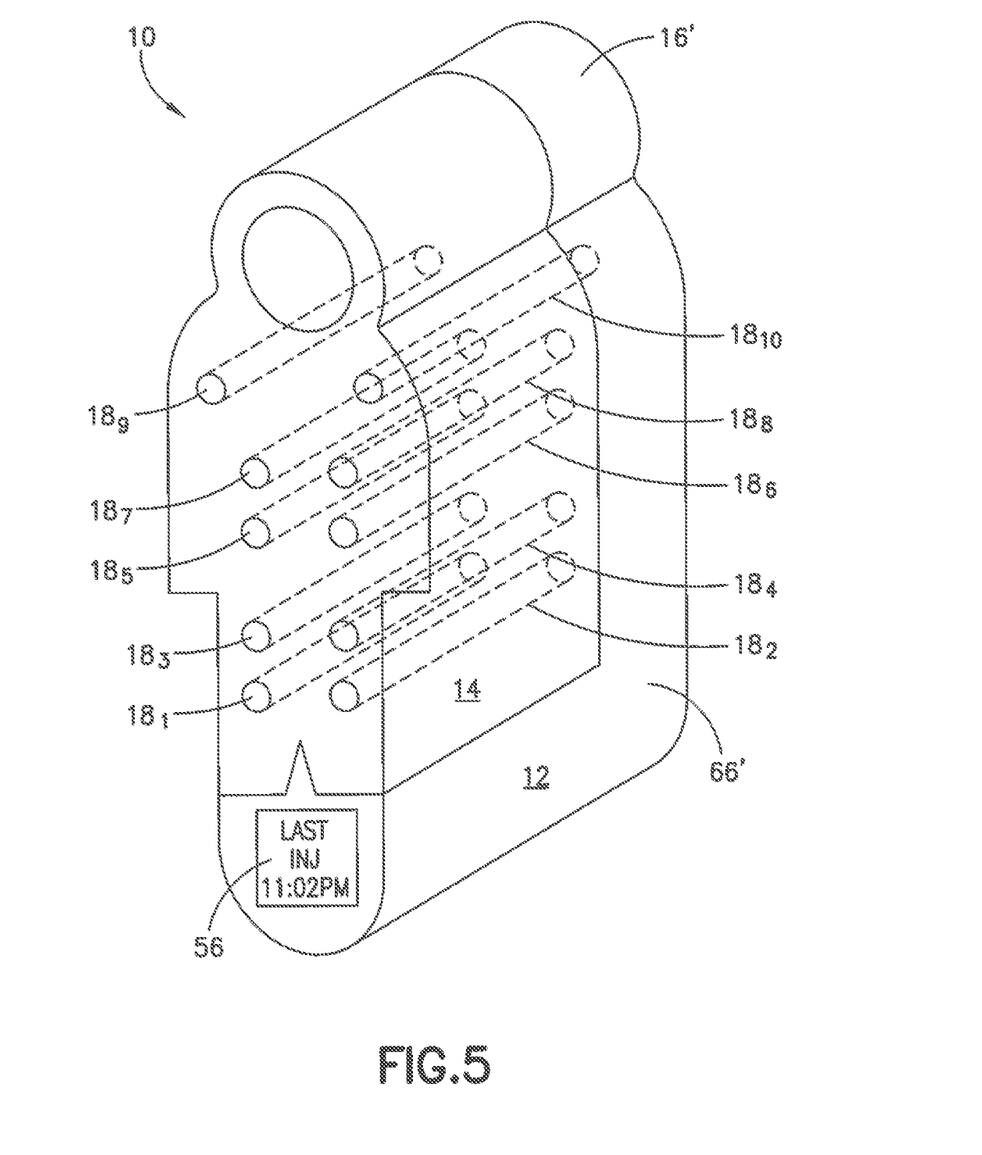
FIG. 5 is a perspective view of a smart dispenser constructed in accordance with another embodiment of the present invention.

As shown in FIGS. 2A and 4, the DCU 12 can be provided with an optional wired interface 58 to which a USB 74 can be selected to receive and store data from the sensors $50_1$-$50_n$ and corresponding time stamps or dates and times of sensor detection of item 20 removal or replacement relative to a cavity 18 or location of the cavity relative to other cavities $18_n$ in the grid. For example, as shown in FIG. 5, the MCC 14 housing 16' can have an anthropomorphic shape rather than a rectangular shape as shown in FIG. 1 in accordance with another example embodiment. The cavities $18_1$-$18_{12}$ in the housing 16' are arranged in a pattern that corresponds to selected injection sites in a patient's body (e.g., cavities $18_1$-$18_4$ corresponding to sites in the patient's legs, cavities $18_5$-$18_8$ corresponding to sites in the patient's abdomen, and cavities $18_9$ and $18_{10}$ corresponding to sites in the patient's upper arms). By using an item 20 (e.g., a pen needle assembly) for injection at a designated injection site represented by its corresponding cavity 18 in the MCC 14, a patient is encouraged to practice injection site rotation among different areas on the body which, in turn, reduces the likelihood of developing lipodystrophy or "lipos." As described below, indicators $80_1$-$80_n$ can be selectively operated by the DCU 12 to encourage site rotation. By storing locations of empty cavities 18 in the memory device 54, the controller 53 can, based on prior detected empty and filled cavities 18, selectively illuminate an indicator 80 to encourage selection of an unused item 20 from the next cavity 18 representing an optimal injection site for site rotation purposes.

Optionally, each cavity 18 has an associated LED 80 which can be programmed to flash or light up to demark a usable injection needle 20. The useable injection needle 20 may be the next free needle, or it may be based on a site rotation algorithm which corresponds to a next safe injection site. In the case of the next safe injection site, it may indicate this by changing the color of the LED. For example:

| LED COLOR | INJECTION SITE |
| --- | --- |
| RED | Thigh |
| BLUE | Abdomen |
| GREEN | Arm |

Alternatively, an LED 80 associated with a cavity 18 can be programmed to indicate next use by a combination of color and flashing (or display on the LCD 56):

| LED COLOR | INJECTION SITE |
| --- | --- |
| RED | RIGHT Thigh |
| BLUE | RIGHT Abdomen |
| GREEN | RIGHT Arm |
| RED Flashing | LEFT Thigh |
| BLUE Flashing | LEFT Abdomen |
| GREEN Flashing | LEFT Arm |

Alternatively it may indicate the next injection site by indicating the next needle and site on the anthropomorphic location on the dispenser shaped like the human body in FIG. 5. It is to be understood that other combinations of color, flashing sequence and indicator locations relative to cavities 18 can be used to indicate cavity 18 status and facilitate item 20 selection.

The DCU 12 can also be provided with an optional wireless interface 60 for connecting the DCU 12 to a wirelessly connected device such as another data store or a mobile phone (e.g., via WiFi, Bluetooth® or cellular network connection). For example, an app can be provided to a user's mobile phone that cooperates with the DCU 12 to provide a representation of the matrix of items 20 in the MCC 14 on the phone display, and programmed indications of which cavities $18_1$-$18_n$ are filled or empty of the items 20, which item 20 to use next, and date and time and location of past item 20 uses (e.g., detected removal of an item from a cavity 18, or detection of an item being removed from and returned to a cavity 18 within a selected time period representing a confirmed use of that item 20 such as a pen needle assembly for administering an injection). An optional button 82 on the DCU 12 can be configured to power the DCU 12 on and off, to wake up the DCU 12 and to request indication of next cavity 18 from which to remove an item 20.

With reference to FIG. 6, a pen 62 with an adapter 60 are shown connected to a pen needle assembly 20 in a cavity 18 of the MCC 14 housing 16. The cavity 18 is depicted with a bullet 24 lining the cavity 18 and enclosing a pen needle assembly 20. As stated above, the cavity 18 can be configured with or without an integral or removable bullet 24. In other words, a cavity 18 can store an item 20 therein without a bullet 24 to line the cavity, or a bullet 24 can be secured in the cavity 18 to line the cavity, or a bullet 24 can be removably provided in a cavity 18 as described above in the example embodiment depicted in FIG. 3. In any of these configurations, the cavity 18 and optional bullet 24 can be configured as a light pipe to facilitate detection of light permitted to enter the cavity 18 from the top thereof upon removal of its item 20, that is, light enters the aperture 23 in the layer 22 of the housing 16 and into the cavity 18. The cavity 18 is dimensioned relative to the item 20 such that the presence of the item 20 in the cavity prevents the light from traveling to the bottom of the cavity and through the layer 30 at the bottom of the housing 16. When the item 20 is removed from the cavity 18, however, the light reflects within the cavity and transmits through the bottom layer 30 of the housing 16 and the surface 68 of the DCU 12 to impinge on a corresponding photosensor 50 in the DCU 12.

As stated above, the housing 16 has a bottom layer 30 that is a sensor transmissible material or at least has sensor transmissible material (e.g., light transmissible material such as a transparent or translucent plastic to allow light in the cavity to impinge on a photosensor 50) in the areas aligned with the cavities $18_1$-$18_n$ and the corresponding sensors $50_1$-$50_n$ in the DCU 12. The degree to which light that has entered an empty cavity 18 will impinge on a corresponding sensor 50 in the DCU 12 can be improved using a lens to focus the light, thereby reducing occurrence of false detections of a filled cavity 18 which can occur when light fails to impinge on a sensor even though the item 20 was removed from the cavity 18 and did not interfere with the path of the light entering the cavity.

Figure 7A:
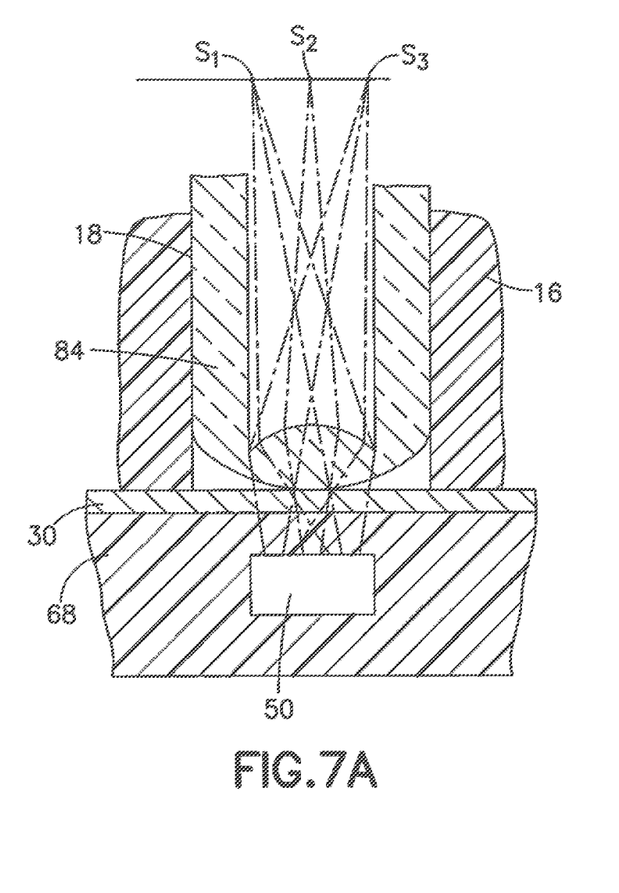
FIGS. 7A and 7B are partial cross-section views of multiple cavity carrier constricted in accordance with respective embodiments of the present invention.
Figure 7B:
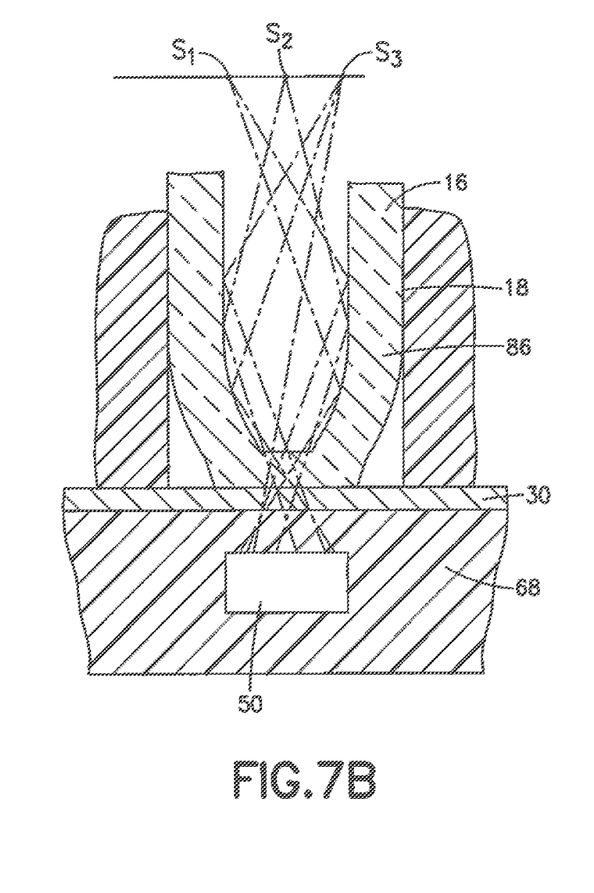

The MCC 14 (e.g., pen needle dispenser) can include a lens integral to the bottom of the plurality of cavities $18_1$-$18_n$, with each cavity lens being optimized to detect the light from the opening at the opposite end of the cavity 18. FIG. 7A depicts a cavity 18 optionally lined with a bullet 24 wherein the bottom of the bullet is configured with a lens 84 shaped to implement the edge-ray principle of non-imaging optics. This lens formation 84 is for dispensers 14 constructed of materials with a low reflectivity, as the lens 84 prefers light transmission through the low reflective housing or bullet material. In accordance with an alternative example embodiment, the bottom of the bullet 24 comprises a lens 86 molded to implement a compound parabolic concentrator. This lens formation 86 is useful for dispensers 14 constructed of materials with a higher reflectivity, since the lens 86 concentrates the more highly reflected light to a central location at the bottom of the cavity. The lenses 84 and 86 can be made from light transmissible material such as a polished acrylic and molded as illustrated in FIGS. 7A and 7B, and molded to the end of a section of the bullet 24 or at the bottom of a cavity 18, wherein the remainder of bullet 24 or cavity can be made from a different material such as a different type of plastic that may not be as effective to focus light but can minimize manufacturing cost. Thus, it is envisioned that the bullet 24 may be manufactured from a single homogeneous material or may be formed in an assembly with multiple materials, or produced in a plural step molding operation from varied materials (e.g. a two-shot molding operation or overmolding operation). It is therefore not required that the lens portion of bullet 24 be of the same material as the functional retrieval portion of bullet 24.

Example operations of the controller 52 of the DCU 12 will now be described with reference to FIG. 8. As stated above, the DCU 12 can be programmed or otherwise configured to track or take inventory of the status of its cavities $18_1$-$18_n$, such as, for example, whether they are empty or filled with an item 20 and from which of the cavities an item should next be removed according to a designated algorithm such as a shot rotation regimen or other pattern of usage from a matrix of items 20 stored in the MCC 14. The controller 52 can begin by noting which of a predetermined number of cavity locations are empty (block 90). The controller then determines if a sensor 50 corresponding to a cavity 18 location detects a new empty cavity (e.g., an item 20 in that cavity has now been removed since the status inventory was taken per block 90), as indicated at block 92. If so, the controller records a time stamp and optionally the date of the removal of the item 20 from the cavity 18 location corresponding to that sensor 50 and records the location within the MCC 14, as indicated respectively in blocks 94 and 96. The controller 52 can begin a timeout loop per block 98 corresponding to a designated duration of time that corresponds to the expected amount of time a user may use the item 20 after removal and then return that item to the cavity (e.g., 10 seconds or other time sufficient for a user to remove an item 20 such as a pen needle assembly from the MCC 14, inject medication and then return the used pen needle assembly back to the same cavity 18 in the MCC 14).

Figure 8:
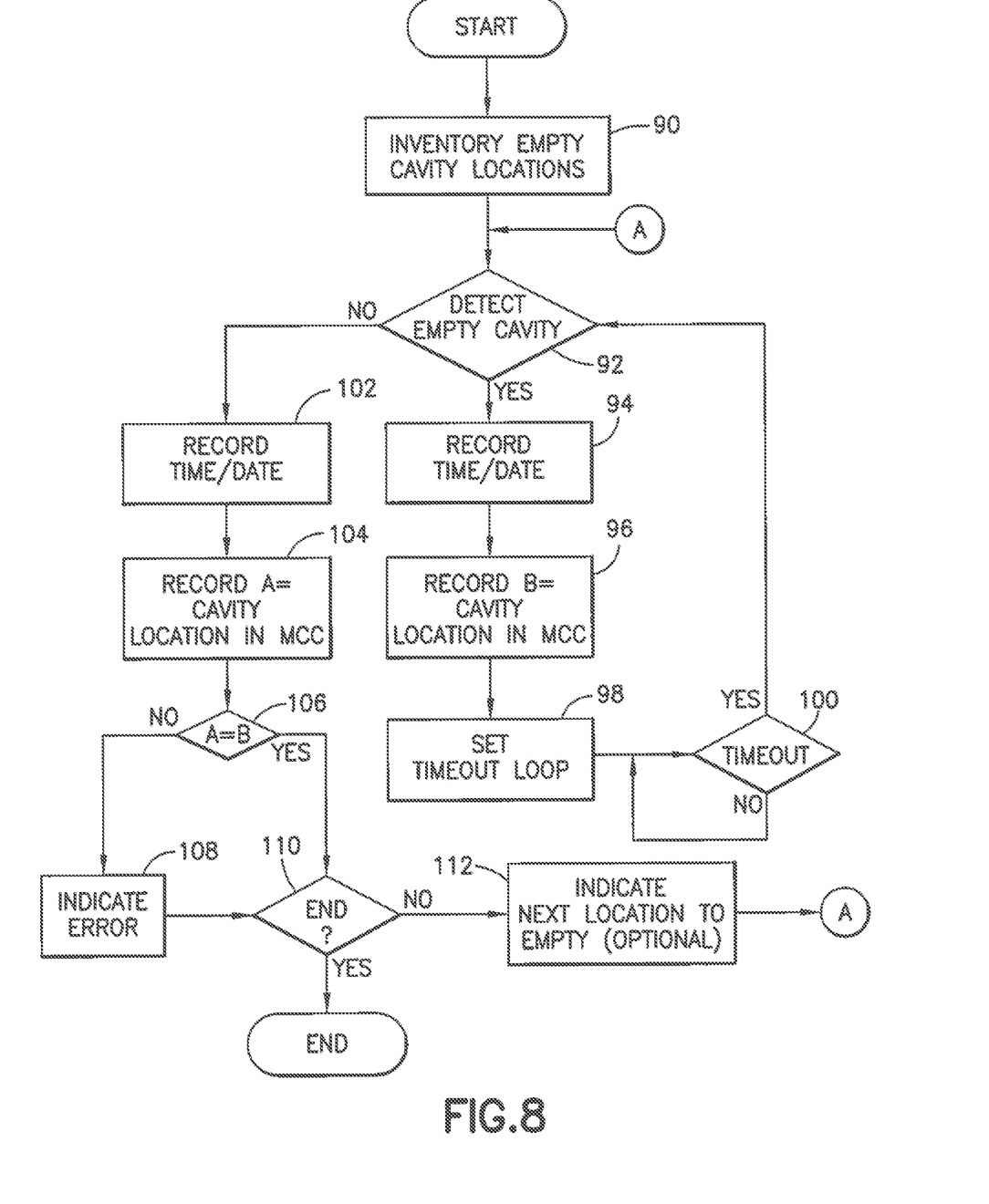
FIG. 8 depicts a sequence of operations for a data collection unit in accordance with an embodiment of the present invention.

After the timeout loop expires per block 100 of FIG. 8, the controller determines if that sensor 50 detects its corresponding cavity 18 being empty. If the item 20 has been returned by the end of the timeout period, the sensor will not detect an empty cavity, as indicated by the negative line from block 92, and will record at least a time stamp for that determination of a filled cavity (block 102) and that cavity's location (block 104). If an item 20 has been detected as successfully removed and replaced, then the locations A and B recorded at blocks 96 and 106 will be the same; otherwise, an error as occurred and an indication of the error can be output (e.g., via the display 56) as indicated in block 108. The DCU 12 can optionally be configured to operate an indicator (e.g., an LED 80) corresponding to a cavity 18 location from which the user should retrieve the next item 20, as described above.

The operations of the controller 52 in the DCU 12 described in connection with FIG. 8 illustrate an example MCC 14 that stores items after use. It is to be understood that operations of the controller 52 can also simply take periodic inventory of the cavity locations to determine which ones are empty, and record time stamps and optional locations of cavities $18_1$-$18_n$ as items 20 are removed therefrom, and therefore not employ a timeout period (blocks 98, 100) or otherwise detect return of the items 20 to their respective cavities (blocks 102, 104).

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments of the present invention can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Method steps can also be performed by, and apparatus of the invention can be implemented as, special purpose logic circuitry, e.g., an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory or ROM (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. A software module may reside in random access memory (RAM), flash memory, ROM, EPROM, EEPROM, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. In other words, the processor and the storage medium may reside in an integrated circuit or be implemented as discrete components.

Computer-readable non-transitory media includes all types of computer readable media, including magnetic storage media, optical storage media, flash media and solid state storage media. It should be understood that software can be installed in and sold with a central processing unit (CPU) device. Alternatively, the software can be obtained and loaded into the CPU device, including obtaining the software through physical medium or distribution system, including, for example, from a server owned by the software creator or from a server not owned but used by the software creator. The software can be stored on a server for distribution over the Internet, for example.

The above-presented description and figures are intended by way of example only and are not intended to limit the present invention in any way except as set forth in the following claims. It is particularly noted that persons skilled in the art can readily combine the various technical aspects of the various elements of the various illustrative embodiments that have been described above in numerous other ways, all of which are considered to be within the scope of the invention.

The invention claimed is:

1. A reusable data collection unit detachably connected to a dispenser, the dispenser having cavities configured to enclose respective items for storage therein and subsequent removal, the data collection unit comprising:
   a base housing detachably connected to the dispenser;
   plural sensors provided on the base housing and configured to detect presence and absence of the items in the respective cavities and generate corresponding sensor data;
   a memory device configured to store the sensor data; and
   a processor provided in the base housing and configured to analyze the sensor data and determine a time stamp of removal of the items from respective ones of the cavities, and
      wherein the processor is configured to analyze the sensor data and determine which of a proposed injection sites have been used based on detection of the absence of items from their corresponding cavities, and select a next proposed injection site based on a designated pattern for using the items on the patient, and generating an indication that indicates which of the items in the cavities to remove from the dispenser and use next on a patient.

2. The reusable data collection unit of claim 1, wherein the processor is configured to analyze the sensor data and determine a dataset comprising at least one of a date and a time of removal of the items from respective ones of the cavities.

3. The reusable data collection unit of claim 1, wherein the processor is configured to analyze the sensor data and determine a dataset comprising at least one of a date and a time of return of the items to respective ones of the cavities.

4. The reusable data collection unit of claim 1, wherein the dispenser is a pen needle magazine dispenser and the items are pen needle assemblies.

5. The reusable data collection unit of claim 1, wherein the cavities are arranged in a designated pattern in the dispenser, and the sensors are arranged in the base housing in a similar pattern to align the sensors with the cavities when the dispenser is connected to the base housing.

6. The reusable data collection unit of claim 1, wherein the plural sensors create a sensor matrix in the base housing, and the cavities in the dispenser are configured in accordance with a grid pattern that corresponds to the sensor matrix.

7. The reusable data collection unit of claim 1, wherein the dispenser has a top separated from a bottom by a wall that defines an outer perimeter of the dispenser, and the cavities each extend from the top toward the bottom of the dispenser,
wherein the outer perimeter defines an anthropomorphic shape, and the cavities are disposed in areas within the anthropomorphic shape that correspond to the proposed injection sites on at least one of the patient's arms, thighs, abdomen and buttock.

8. The reusable data collection unit of claim 7, wherein the indication is at least one of a designated color and a flash of a light-emitting diode (LED).

9. The reusable data collection unit of claim 7, wherein a bottom of the dispenser comprises at least one transparent area that is aligned with at least one of the cavities, the corresponding one of the sensors aligned with the cavity being operable to detect ambient light that enters the cavity via the at least one transparent area when the corresponding item is removed from the cavity.

10. The reusable data collection unit of claim 1, wherein the sensor data is transmitted from the reusable data collection unit to a remote device using at least one of a universal serial bus (USB) connector and a wireless link.

11. A medical instrument dispensing device having a reusable data collection unit detachably connected to a dispenser, the dispenser having cavities configured to house a plurality of sterile medical instruments for storage therein and subsequent removal, the data collection unit comprising:
a base housing detachably connected to the dispenser;
plural sensors provided on the base housing and configured to detect presence and absence of each of the plurality of sterile medical instruments in the corresponding cavity and generate corresponding sensor data;
a memory device configured to store the sensor data; and
a processor provided in the base and configured to analyze the sensor data and determine a dataset to characterize the removal of at least one of the plurality of sterile medical instruments from its corresponding cavity,
wherein the processor is configured to analyze the sensor data and determine which of a proposed use sites have been used based on detection of the absence of items from their corresponding cavities, and select a next proposed use site based on a designated pattern for using the items on the patient, and generating an indication that indicates which of the medical instruments in the cavities to remove from the dispenser and use next on a patient.

12. The reusable data collection unit of claim 11, wherein the processor is configured to analyze the sensor data and determine a dataset comprising at least one of a date and a time of removal of the plurality of sterile medical instruments from its corresponding cavity.

13. The reusable data collection unit of claim 11, wherein the processor is configured to analyze the sensor data and determine a dataset that comprises at least one of a date and a time of return of the medical instruments to its corresponding cavity.

14. The reusable data collection unit of claim 11, wherein the dispenser is a pen needle magazine dispenser and the plurality of sterile medical instruments are pen needle assemblies.

15. The reusable data collection unit of claim 11, wherein the dispenser has a top separated from a bottom by a wall that defines an outer perimeter of the dispenser, and the cavities each extend from the top toward the bottom of the dispenser,
wherein the outer perimeter defines an anthropomorphic shape, and the cavities are disposed in areas within the anthropomorphic shape that correspond to the proposed use sites on the patient's body.

* * * * *